United States Patent
Torres Luque et al.

(10) Patent No.: US 10,488,389 B2
(45) Date of Patent: Nov. 26, 2019

(54) SYSTEM FOR ASSESSING CHLORIDE CONCENTRATION AND CORRESPONDING METHOD AND SENSOR

(71) Applicants: UNIVERSITÉ DE NANTES, Nantes (FR); CENTRE NATIONAL DE LA RECHERCHE SCIENTIFIQUE-CNRS, Paris (FR); UNIVERSIDAD DE LOS ANDES, Bogota (CO)

(72) Inventors: Magda Marcela Torres Luque, Bogota (CO); Johann Faccelo Osma Cruz, Bogota (CO); Mauricio Sanchez Silva, Bogota (CO); Emilio Bastidas Arteaga, Nantes (FR); Franck Schoefs, Sucé sur Erdre (FR)

(73) Assignees: UNIVERSITÉ DE NANTES, Nantes (FR); CENTRE NATIONAL DE LA RECHERCHE SCIENTIFIQUE—CNRS, Paris (FR); UNIVERSIDAD DE LOS ANDES, Bogota (CO)

( * ) Notice: Subject to any disclaimer, the term of this patent is extended or adjusted under 35 U.S.C. 154(b) by 53 days.

(21) Appl. No.: 15/743,053

(22) PCT Filed: Jul. 7, 2016

(86) PCT No.: PCT/EP2016/066212
§ 371 (c)(1),
(2) Date: Jan. 9, 2018

(87) PCT Pub. No.: WO2017/005885
PCT Pub. Date: Jan. 12, 2017

(65) Prior Publication Data
US 2019/0107525 A1    Apr. 11, 2019

(30) Foreign Application Priority Data

Jul. 9, 2015 (EP) ................................ 15306128

(51) Int. Cl.
| | | |
|---|---|---|
| G01R 27/26 | (2006.01) | |
| G01N 33/38 | (2006.01) | |
| G01N 17/02 | (2006.01) | |
| G01N 27/04 | (2006.01) | |
| G01N 27/20 | (2006.01) | |
| G01N 27/24 | (2006.01) | |

(52) U.S. Cl.
CPC ........... *G01N 33/383* (2013.01); *G01N 17/02* (2013.01); *G01N 27/041* (2013.01); *G01N 27/20* (2013.01); *G01N 27/24* (2013.01)

(58) Field of Classification Search
CPC ........ G01N 27/20; G01N 27/24; G01N 27/26; G01N 27/021; G01N 27/041;
(Continued)

(56) References Cited

U.S. PATENT DOCUMENTS 4,921,591 A * 5/1990 Mochizuki ......... G01N 27/3335
204/412
5,472,590 A * 12/1995 Yamashita ......... G01N 27/3335
204/403.13

(Continued)

OTHER PUBLICATIONS

Torres-Luque, M., et al., "Non-Destructive Methods for Measuring Chloride Ingress into Concrete: State-of-the-Art and Future Challenges," Construction and Building Materials 2014;68:68-81.
(Continued)

*Primary Examiner* — Thang X Le
(74) *Attorney, Agent, or Firm* — Kenealy Vaidya LLP

(57) ABSTRACT

Some embodiments are directed to a system for assessing chloride concentration at one predetermined area of a porous or composite material, such as a reinforced concrete structure, including a sensor embedded in the predetermined area of the material, an analyzer connected to the sensor, and a processing module connected to the analyzer. The sensor
(Continued)

includes two facing or coplanar electrodes, an intermediate layer arranged between the electrodes, the intermediate layer being in contact with the material of the predetermined area of the structure and including calcium aluminates. The analyzer is configured to apply an alternate current between the electrodes and output an impedance value or capacitance value of the intermediate layer. The processing module is configured to compute a chloride concentration assessment in the predetermined area of the material based on the impedance value or capacitance value outputted by the analyser.

20 Claims, 7 Drawing Sheets

(58) Field of Classification Search
CPC ............... G01N 27/302; G01N 27/333; G01N 27/3335; G01N 27/4167; G01N 27/4162; G01N 27/4163; G01N 27/4045; G01N 27/414; G01N 22/383; G01R 29/12
See application file for complete search history.

(56) References Cited

U.S. PATENT DOCUMENTS

| | | | | |
|---|---|---|---|---|
| 5,505,836 A * | 4/1996 | Miyahara | ........... | G01N 27/3335 204/416 |
| 6,767,450 B2 * | 7/2004 | Terashima | ........... | G01N 27/333 204/409 |
| 7,063,781 B2 * | 6/2006 | Murray | .............. | G01N 27/3335 204/404 |
| 2004/0118682 A1 * | 6/2004 | Murray | .............. | G01N 27/3335 204/418 |
| 2007/0045128 A1 * | 3/2007 | Krafthefer | ........... | G01N 27/333 205/778.5 |
| 2009/0071826 A1 * | 3/2009 | Kamahori | .......... | G01N 27/3335 204/418 |
| 2014/0209485 A1 * | 7/2014 | Ohgami | ............... | G01N 27/333 205/789 |
| 2014/0251805 A1 * | 9/2014 | Salzillo | ................ | G01N 27/302 204/406 |
| 2015/0153399 A1 * | 6/2015 | Miyazawa | ........... | G01N 27/021 324/457 |
| 2016/0195491 A1 * | 7/2016 | Rao | ....................... | G01N 27/333 204/411 |

OTHER PUBLICATIONS

Jin, M., et al., "Investigation on the Performance Characteristics of Chloride Selective Electrode in Concrete," Ionics 2015;21(10):2981-2992.

International Search Report and Written Opinion for PCT Patent App. No. PCT/EP2016/066212 (dated Oct. 13, 2016).

European Search Report for European Patent App. No. 15306128.8 (dated Dec. 3, 2015).

* cited by examiner

SYSTEM FOR ASSESSING CHLORIDE CONCENTRATION AND CORRESPONDING METHOD AND SENSOR

CROSS REFERENCE TO RELATED APPLICATION(S)

This application is a national phase filing under 35 C.F.R. § 371 of and claims priority to PCT Patent Application No. PCT/EP2016/066212, filed on Jul. 7, 2016, which claims the priority benefit under 35 U.S.C. § 119 of European Patent Application No. 15306128,8, filed on Jul. 9, 2015, the contents of each of which are hereby incorporated in their entireties by reference.

BACKGROUND

Some embodiments relate generally to the field of material durability and more specifically to the assessment of chloride concentration in porous and composite materials, such as reinforced concrete, pre-stressed concrete or mixed steel-concrete structures. More particularly, some embodiments relate to a system and a method for assessing chloride concentration in a predetermined area of a porous or composite material and to a sensor used in this system and method.

Chloride ingress is one of the major factors of reinforced concrete (RC) deterioration affecting structural serviceability and safety. Chloride ions are accelerators of corrosion processes on the rebar surfaces, decreasing the lifetime of the structures. For other materials, the detection of chlorides is an indicator of the waterproofing against seawater or material durability.

Chloride-induced corrosion begins when the concentration of chloride at the steel bars reaches a threshold value that destroys a thin passive layer of corrosion products (caused by the high alkalinity of concrete at the end of construction), which protects steel bars against corrosion. After corrosion initiation, there is a premature deterioration caused by various mechanisms: loss of reinforcement section, loss of steel-concrete bond, concrete cracking and delamination. After steel corrosion starts, the RC physical and mechanical properties decay at rate that depends on the environmental conditions. This deterioration process generates larger repair and maintenance costs with severe impact on the durability and life-cycle performance.

The measurement of chloride content at the concrete cover could be used to estimate the risk of corrosion initiation, and therefore, to enhance or optimize repair and maintenance costs.

The ingress phenomenon of the chloride ions into the concrete is very complex since it depends on many parameters, notably the concrete composition, its cracking state and the climate to which it is exposed.

SUMMARY

Over the past 30 years, different techniques for chloride measuring have been developed, some of them being destructive and invasive, others being non-destructive. Some of them can be even used in situ. These last ones are desirable techniques for maintenance and prediction of RC structures durability.

The most popular techniques are potentiometric and Volhard methods. They measure free and total chlorides in concrete cores extracted from in service structures. However, these techniques are mostly semi-destructive, time-consuming and costly. Furthermore, their destructive nature leads to additional indirect costs such as traffic delay, traffic management, road closures and lost productivity, which increase costs further. Moreover the destructive nature makes difficult a measure of the evolution at the same place on site or in the same sample in lab.

Non-destructive techniques (NDT) also exist. They imply methods that do not change the environment and the futures usefulness of the material where the measurement is taken. These techniques work for example with external or embedded equipment. The most studied and developed general methods could be classified into three types:
(i) ion selective electrodes (ISE),
(ii) electrical resistivity (ER), and
(iii) optical fiber sensor (OFS).

These three NDT types are reviewed in "Non-destructive methods for measuring chloride ingress into concrete: State-of-the-art and future challenges", M. Torres-Luque, E. Bastidas-Arteaga, F. Schoefs, M. Sanchez-Silva, J. F. Osma, Construction and Building Material, Volume 68, pp 68-81, 2014.

ISE, ER and OFS have shown some advantages: ISE shows a good chemical stability in aggressive environments, ER is sensitive to chloride presence, and OFS shows better sensitivity to chlorides than the others. However, there are some problems that have not been solved yet. For instance, most of these methods are very sensitive to changes in the conditions inside the concrete structure (e.g., changes in temperature, relative humidity, pH), and some of them require a careful calibration process.

More specifically, ISE is very sensitive to the position of the electrodes and to alkalinity and temperature. In addition, the durability of the reference electrode is not adapted to the lifetime of the concrete structure. ER is very sensitive to the water content of the concrete, the steel bars presence, the carbonation and the presence of electromagnetic fields. Finally, OFS is theoretically adapted to measure low values and it is less impacted by environmental factors but the optical fiber is fragile and needs an additional sheath to be isolated from the concrete that is a corrosive medium.

It may therefore be beneficial to provide a measurement method that is non-destructive and that alleviates at least partially the drawbacks of the related art NDT techniques.

Some embodiments therefore use a new type of sensor embedded in the porous or composite material (for example the reinforced concrete structure), this sensor including a calcium aluminate layer adapted for collecting, detecting and measuring free chloride ions coming from the porous or composite material. The collection of free chloride ions by the above-mentioned layer causes changes in the electrical properties of the layer, notably the impedance and the relative permittivity of the layer. The chloride concentration of the porous or composite material in the proximity of the sensor can therefore be assessed based on the impedance and the relative permittivity changes of the layer of the sensor. This sensor is integrated into a system configured to measure these impedance and relative permittivity changes of the layer and to compute on the basis of these changes a chloride concentration assessment of the porous or composite material in the vicinity of the sensor.

More specifically, some embodiments are directed to a system for assessing chloride concentration at one predetermined area of a porous or composite material, such as a reinforced concrete structure, including:
a sensor embedded in the predetermined area,
an analyzer connected to the sensor, and
a processing module connected to the analyzer, wherein the sensor includes two facing or coplanar electrodes, called electrodes, an intermediate layer arranged between the electrodes, the intermediate layer being in contact with the material of the predetermined area and including calcium aluminates, wherein the analyzer is configured to apply an alternate current between the electrodes and output an impedance value or capacitance value of the intermediate layer, and wherein the processing module is configured to compute a chloride concentration assessment in the predetermined area based on the impedance value or capacitance value outputted by the analyzer.

In a first embodiment, the electrodes are facing electrodes and the analyzer is configured to output a capacitance value. For computing the chloride concentration assessment in the predetermined area, the processing module is configured to compute a relative permittivity value of the intermediate layer between the electrodes from the capacitance value outputted by the analyzer and to compute the chloride concentration assessment in the predetermined area based on the computed relative permittivity value.

In this embodiment, the frequency of the alternate current is possibly or preferably included in [100 Hz, 5 MHz].

In a second embodiment, the analyzer is configured to measure an impedance value between the coplanar electrodes, by applying an alternate current between these electrodes and the processing module is configured to compute the chloride concentration assessment in the predetermined area based on the measured impedance value.

In this embodiment, the electrodes are possibly or preferably coplanar electrodes. In addition, the frequency of the alternate current is included in the frequency range [100 Hz, 100 kHz] and preferably in one of the following groups of frequency ranges: [16 kHz, 37.5 kHz]; [52 kHz, 65 kHz]; [81 kHz, 99 kHz].

Some embodiments are directed to a method for assessing chloride concentration in a predetermined area of a porous or composite material, such as a reinforced concrete structure, by using a sensor embedded in the predetermined area, the sensor including two facing or coplanar flat electrodes, an intermediate layer arranged between the two electrodes, the intermediate layer being in contact with the material of the predetermined area and including calcium aluminates, the method including:

measuring a capacitance value or an impedance value of the intermediate layer by applying an alternate current between the electrodes; and computing a chloride concentration assessment in the predetermined area based on the measured impedance value or capacitance value.

In a first embodiment, the electrodes are facing electrodes and the measured value is a capacitance value of the intermediate layer between these facing electrodes, and the chloride concentration assessment is computed by:

computing a relative permittivity value of the intermediate layer between the electrodes, and computing the chloride concentration assessment in the predetermined area based on the computed relative permittivity value.

In this embodiment, the frequency of the alternate current is preferably included in [100 Hz, 5 MHz].

In a second embodiment, the measured value is an impedance value of the intermediate layer between the electrodes, and the chloride concentration assessment is computed based on the measured impedance value.

In this embodiment, the electrodes are possibly or preferably coplanar electrodes. In addition, the frequency of the alternate current is included in the frequency range [100 Hz, 100 kHz] and possibly or preferably in one of the following groups of frequency ranges: [16 kHz, 37.5 kHz]; [52 kHz, 65 kHz]; [81 kHz, 99 kHz].

Finally, some embodiments are directed to a chloride sensor to be embedded in a predetermined area of a porous or composite material, such as a reinforced concrete structure, including:

a housing, at least two facing or coplanar flat electrodes within the housing, an intermediate layer arranged between the electrodes within the housing, the intermediate layer being in contact, via at least one hole in the housing, with the material of the predetermined area and including calcium aluminates, and pin connectors connected to the electrodes via conductive lines and arranged for connecting the electrodes to an external device.

In a particular embodiment, the sensor includes a plurality of pairs of electrodes offset with respect to one another along an axis of the sensor and connected to a plurality of pin connectors, an intermediate layer being arranged between the electrodes of each pair of electrodes and at least a hole being arranged in the housing at the proximity of each pair of electrodes and opening into the intermediate layer.

In a particular embodiment, the calcium aluminates are selected among CA (=CaO.Al$_2$O$_3$), C$_3$A (=3(CaO).Al$_2$O$_3$) and C$_{12}$A$_7$ (=12(CaO).7(Al$_2$O$_3$)).

In a particular embodiment, the material of the housing is fiber glass or Bakelite or ceramic or Teflon.

BRIEF DESCRIPTION OF THE DRAWINGS

The invention can be better understood with reference to the following description and drawings, given by way of example and not limiting the scope of protection, and in which.

DETAILED DESCRIPTION OF EXEMPLARY EMBODIMENTS

Figure 1:
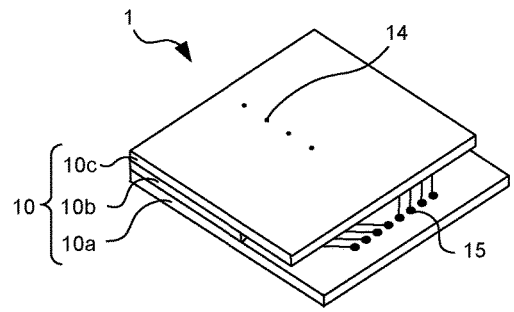
FIG. 1 is a perspective view of an embodiment of a chloride sensor according to the invention.
Figure 2:
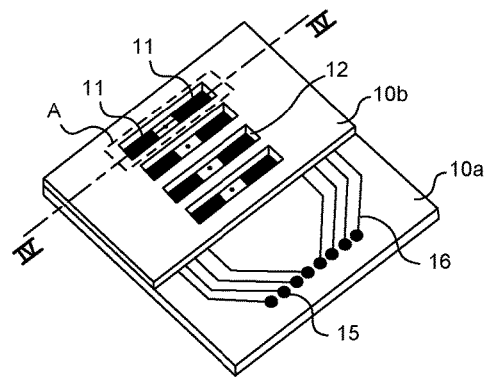
FIG. 2 is a partial perspective view of the sensor of FIG. 1.
Figure 3:
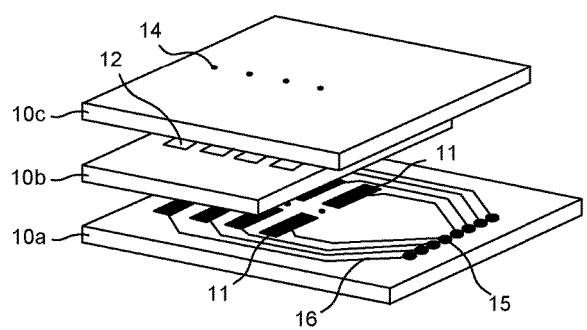
FIG. 3 is an exploded view of the sensor of FIG. 1.
Figure 4:
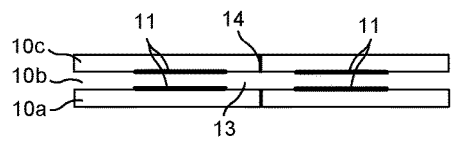
FIG. 4 is a vertical cross-section view along the axis IV-IV of FIG. 1.

Some embodiments will be described hereinafter for a concrete structure, such as a reinforced, pre-stressed or mixed steel-concrete. Of course, the invention can be applied to other porous or composite materials.

While example embodiments are capable of various modifications and alternative forms, embodiments thereof are shown by way of example in the drawings and will herein be described in details. It should be understood, however, that there is no intent to limit example embodiments to the particular forms disclosed, but on the contrary, example embodiments are to cover all or most modifications, equivalents, and alternatives falling within the scope of the claims. Like numbers refer to like elements throughout the description of the figures.

Before discussing example embodiments in more details, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figures. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a storage medium. A processor(s) may perform the necessary tasks. Specific structural and functional details disclosed herein are merely representative for purposes of describing example embodiments of the present invention. This invention may, however, be embodied in many alternate forms and should not be construed as limited to only the embodiments set forth herein.

The terminology used herein is for the purpose of describing particular embodiments only and is not intended to be limiting of example embodiments. As used herein, the singular forms "a", "an" and "the" are intended to include the plural forms as well, unless the context clearly indicates otherwise. It will be further understood that the terms "includes" and/or "including", when used herein, specify the presence of stated features, integers, steps, operations, elements and/or components, but do not preclude the presence or addition of one or more other features, integers, steps, operations, elements, components and/or groups thereof. Similarly, it is to be noticed that the term "coupled" should not be interpreted as being restricted to direct connections only. Thus, the scope of the expression "a device A coupled to a device B" should not be limited to devices or systems wherein an output of device A is directly connected to an input of device B. It means that there exists a path between an output of device A and an input of device B which may be a path including other devices or means. Unless otherwise defined, all or most terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Some embodiments are directed to a novel embedded sensor including a specific layer reacting with free chloride ions coming from the concrete structure, this reaction causing modifications in the electrical properties (impedance, conductivity and relative permittivity) of the layer. The amount of chloride that ingress in the sensor can therefore be estimated through the electrical properties' changes. According to some embodiments, the specific layer includes calcium aluminate.

FIGS. 1 to 5 illustrate an embodiment of the sensor according to the invention.

The Chloride sensor 1 includes a housing 10 made of three parts 10a, 10b and 10c. Since the sensor is deemed to be imbedded in the concrete, it should be able to face the environment inside the concrete (temperature, humidity, residual inner forces of the concrete). Strong materials that can withstand the environmental conditions are required for the housing. In a possible or preferred embodiment, the housing 10 has a matrix of fiber glass that, in general, shows good physical and chemical properties. Other materials like Bakelite or Teflon can be used.

More specifically, the housing 10 includes a lower part 10a, an intermediate part 10b and an upper part 10c. The lower and upper parts 10a and 10c are printed circuit boards (PCBs). Conductive electrodes 11, in copper or gold material, are printed on the lower surface of the upper part 10c and on the upper surface of the lower part 10a. Holes 12 are made in the intermediate part 10b and are filled with a powder of calcium aluminate forming a calcium aluminate layer 13. In this embodiment, the shape of the electrodes 11 and the holes 12 is rectangular.

The electrodes 11 and the holes 12 are positioned relative to each other such that, when the three parts are assembled together, each electrode 11 of the upper part 10c is facing an electrode 11 of the lower part 10b, the calcium aluminate layer of a hole 12 being placed between the two electrodes.

In the embodiment illustrated by the FIGS. 1 to 5, the sensor includes eight pairs of facing electrodes 11 and four holes filled with a calcium aluminate layer. The eight pairs of facing electrodes are distributed into fours rows of two pairs of facing electrodes and two columns of four pairs of facing electrodes, one hole 12 (forming a chamber) filled with a calcium aluminate layer being associated to each row of pairs of facing electrodes.

In these figures, two pairs of facing electrodes 11 are associated to the same hole 12 (or chamber) such that a same calcium aluminate layer 13, so-called intermediate layer, is present between the electrodes of these two pairs of electrodes.

Holes 14 are made in the upper part 10c and/or the lower part 10a such that, when the sensor is embedded in the concrete structure, the intermediate layer 13 is in contact with the concrete via the holes 14. In the illustrated embodiment, one hole 14 in the upper part 10c and one hole 14 in the lower part 10a are made for each row of facing electrodes and open into one hole 12 of the intermediate part. In each part 10a or 10c, the holes 14 are offset horizontally with respect to one another in order to be in contact staggered areas of the concrete. Each hole 14 is centred between the coplanar electrodes 11.

Additionally, each electrode 11 of the upper part and the lower part is connected to a pin connector 15 via a conductive line 16. These pin connectors are deemed to connect the electrodes 11 to external devices.

As mentioned above, each hole 12 is filled a powder including calcium aluminates. The powder is for example of a powder including monocalcium aluminates CA (=CaO.Al$_2$O$_3$) or tricalcium aluminates C$_3$A (=3(CaO).Al$_2$O$_3$) or C$_{12}$A$_7$ or a powder including a mix of the calcium aluminates.

Figure 5:
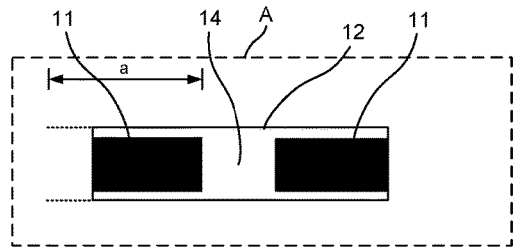
FIG. 5 is an enlarged view of a detail A of FIG. 2.

FIG. 5 is a view illustrating the size of different elements of the sensor that will be tested later in the present description. The size of the rectangular hole 12 in the intermediate part is c*d and the size of the rectangular electrodes is a*b. Only a portion a'*b of the electrode 11a is exposed to the intermediate layer present in the hole 12. The hole 14 is circular and its diameter is 6 Angströms ($10^{-10}$ m). This diameter is greater than the diameter of a water molecule (few Angströms), the diameter of chloride ions (few Angströms) and the diameter of the concrete's pores (about 1000 Angströms). Thus water molecules and chloride ions can go inside the sensor or reach the intermediate layer via the hole 14.

Figure 6:
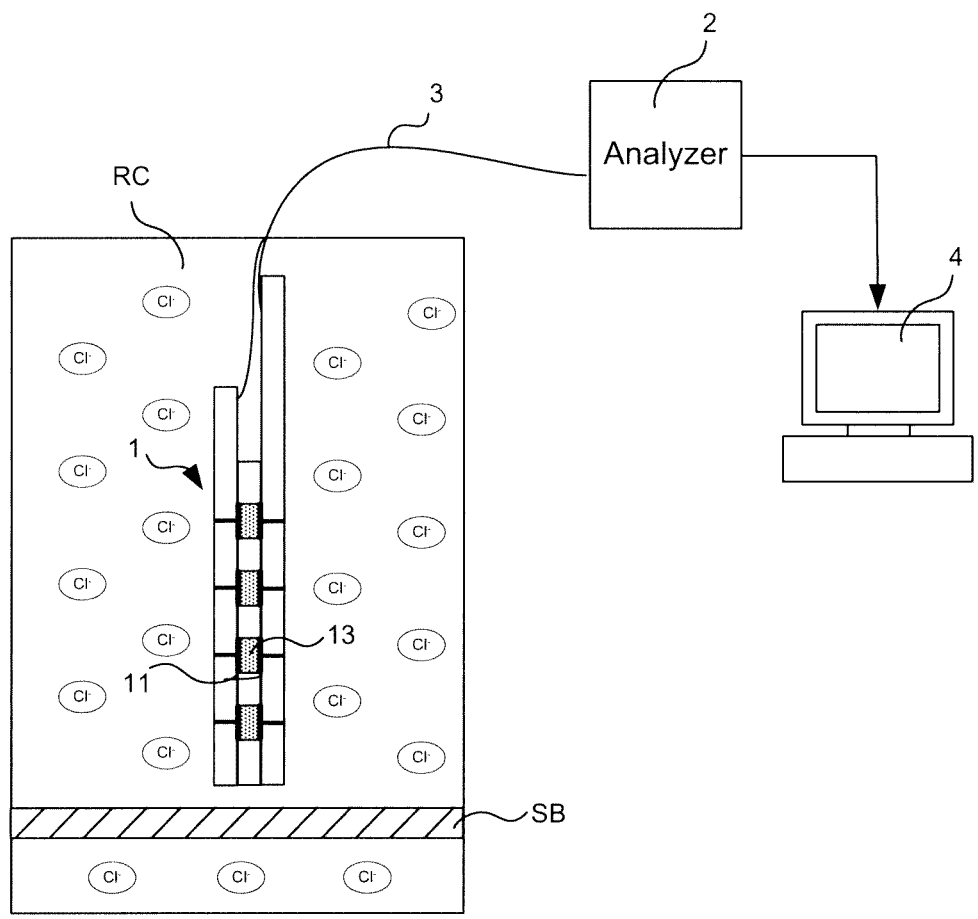
FIG. 6 is an schematic view of a system according to the invention.

As can be seen on FIG. 6, this sensor 1 is intended to be imbedded into a reinforced concrete structure RC including a steel bar SB. The sensor 1 is imbedded vertically in the RC structure, perpendicularly to the external wall of the RC structure, in order to measure the chloride concentrations at different depths in the RC structure. In a variant, it can be placed horizontally to measure chloride content in a specific depth.

These measures are carried out by connecting the sensor 1 to an analyzer 2 via connexion lines 3. The analyzer 2 is connected to a processing module 4.

In a first embodiment of the invention, the chloride concentration assessment is computed based on the capacitance of the intermediate layer between two facing electrodes. In this embodiment, the analyzer 2 is a capacitance analyzer.

In a second embodiment of the invention, the chloride concentration assessment is computed based on the impedance value of the intermediate layer between two facing or coplanar electrodes. In this second embodiment, the analyzer 2 is an impedance analyzer.

These two embodiments will be described in more detail hereinafter.

First Embodiment

Figure 7:
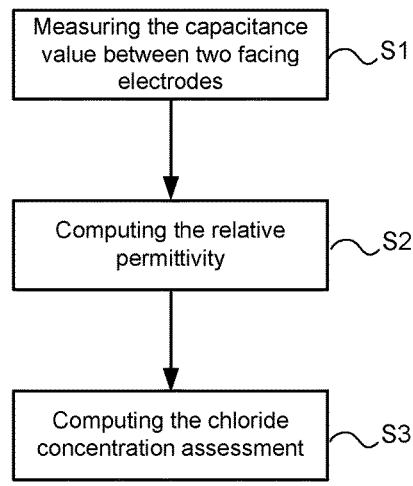
FIG. 7 is a flow chart of the successive steps of first method according to the invention.

In this embodiment, the method for assessing the chloride concentration using the above described sensor is detailed in the flow chart of FIG. 7.

In a first step, S1, the capacitance value C between each pair of facing electrodes 11 of the sensor 1 is measured. The capacitance value is measured by applying an alternate current between the electrodes. This capacitance value is measured by the analyzer 2.

In a second step, S2, a relative permittivity value $\varepsilon_r$ is computed from the capacitance value C with the following equation:

$$\varepsilon_r = \frac{1}{\varepsilon_0} \cdot C \cdot \frac{d}{S} \tag{1}$$

where:
$\varepsilon_0$ is the vacuum permittivity ($\varepsilon_0$=8.85×$10^{-12}$ F/m);
d is the distance between the two electrodes, and
S is the area of the electrodes exposed to calcium aluminate layer (S=a'*b).

This relative permittivity value $\varepsilon_r$ is computed by the analyzer 2 and/or the processing module 4.

In a third step, S3, the chloride concentration assessment is computed by the processing module 4 based on the relative permittivity value $\varepsilon_r$.

In this embodiment, the analyzer 2 is for example the analyzer Agilent 4294A coupled to Dielectric text fixture 16451B. For this specific device, the capacitance can be directly measured, applying an alternate current at frequency range of 100 Hz-5 MHz, with maximum voltage of 0.5V.

This method has been experimented by using a sensor as illustrated by FIGS. 1 to 5. The area S of the electrodes exposed to the intermediate layer 13 is 1.13×$10^{-3}$ m$^2$. The experiments are realized at a temperature of 19° C.±1° C. The intermediate layer 13 is done by putting 6.6 g of Monocalcium aluminate powder (CA) in each hole (chamber) 12 and by tamping with a rammer during 120 seconds until it reaches a thickness between 1.84×$10^{-3}$ m and 2.27×$10^{-3}$ m.

Water deionized (0M) and three NaCl solutions with three different NaCl concentrations were used to test the dielectric behaviour of the monocalcium aluminate layer (CA layer): 0.5M, 0.7M and 1.0M.

Table 1 lists the name and characteristics of each test.

TABLE 1

| Sample name | NaCl Concentration (M—Molar) | NaCl Concentration (% w of Cl$^-$/w of total solution) |
| --- | --- | --- |
| CA | 0 (Dried) | 0 |
| CAH | 0 (Hydrated) | 0 |
| CACl0.5 | 0.5 | 0.0257 |
| CACl0.7 | 0.7 | 0.0357 |
| CACl1 | 1.0 | 0.0486 |

In addition, measurements were performed 1 minute after 1 ml (millilitre) of NaCl solution is added to CA and every 10 minutes for 1 hour to determine time-dependency. Each experiment was performed by triplicate. The NaCl solutions were introduced in the sensor by the holes 14.

Figure 8:
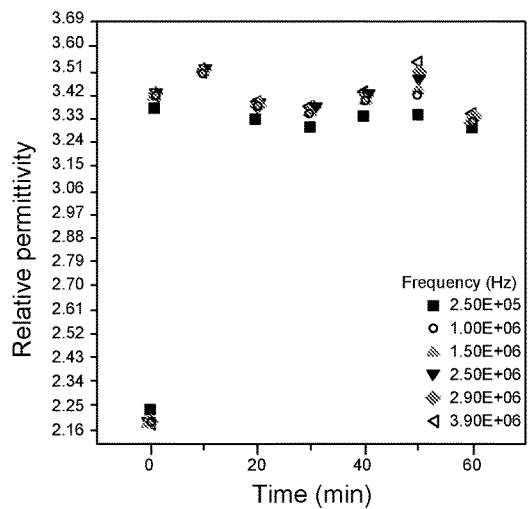
FIG. 8 shows curves illustrating, for different frequencies, the relative permittivity of a CA layer versus time when 0.7M NaCl solutions are added to CA layer at regular times.

FIG. 8 shows diagrams representing the computed relative permittivity versus Time of a CA layer when 1 ml of 0.7M NaCl solution is added every 10 minutes and for different frequencies of alternate current. At the beginning, the CA layer is dried.

All or most of these diagrams show the same tendency. In the first 10 minutes of each experiment, the relative permittivity reaches a steady value and remains approximately at this value until the end of the measurement period. These diagrams suggest that relative permittivity does depend on neither the time nor the frequency in this frequency range.

Figure 9:
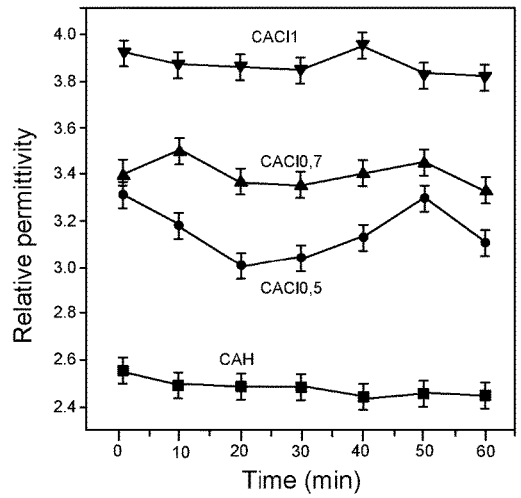
FIG. 9 shows curves illustrating, for different concentrations of NaCl solutions, the relative permittivity of a CA layer versus time.

FIG. 9 shows the change in relative permittivity as chloride solution concentration is increased. The effect of chloride solutions is to increase the measured relative permittivity. It means that capacitance between the electrodes arises due to the ingress of Cl and Na ions that caused an ionic polarization inside the material.

Figure 10:
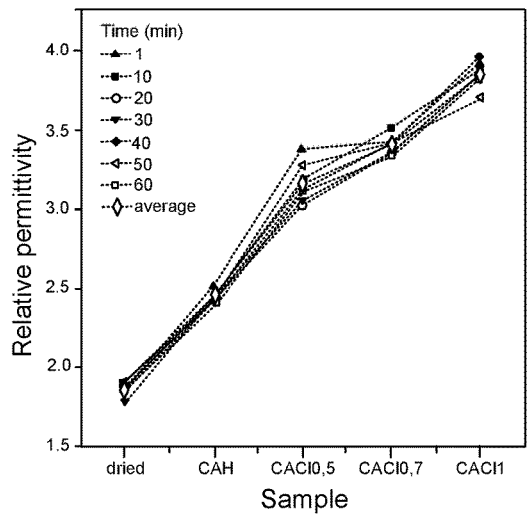
FIG. 10 shows curves illustrating the relative permittivity of a CA layer for different concentrations of NaCl solutions and different times.
Figure 11:
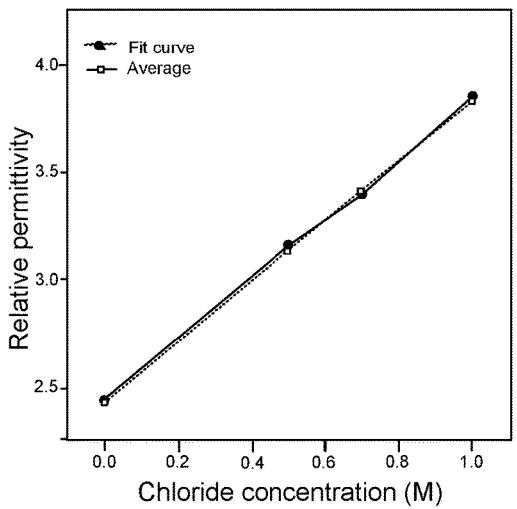
FIG. 11 shows curves illustrating the relative permittivity of a CA layer versus the chloride concentration.

FIGS. 10 and 11 show that relative permittivity $\varepsilon_r$ of the CA layer is proportional to its chloride concentration through the following relation:

$$\varepsilon_r = 2.438 + 1.391 X \quad (1)$$

where: $\varepsilon_r$ is the relative permittivity and X is the molar chloride concentration.

More specifically, FIG. 10 shows the effect of chloride content on the measured relative permittivity for CA dried and for CA exposed to 0M, 0.5M, 0.7M and 1M NaCl solutions and FIG. 11 shows the correlation between chloride concentration and relative permittivity.

It means that ionic polarization of NaCl and molecular polarization of $H_2O$ lead to higher values of the dielectric constant allowing the increased of stored charge in the CA. Also, ionic penetration into the material causes that electric resistivity decreases, and of course, conductivity increases.

Second Embodiment

Figure 12:
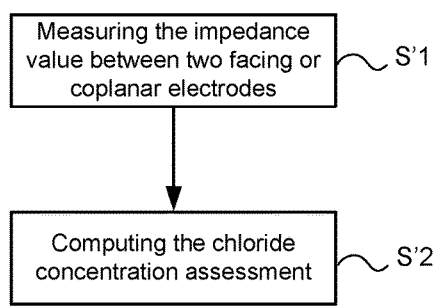
FIG. 12 is a flow chart of the successive steps of second method according to the invention.

In this embodiment, the method for assessing the chloride concentration using the above described sensor is detailed in the flow chart of FIG. 12.

In a first step, S'1, an impedance value between each pair of facing or coplanar electrodes 11 of the sensor 1 is measured. The impedance value is measured by applying an alternate current between the two electrodes. This impedance value is measured by the analyzer 2.

In a second step, S'2, the chloride concentration assessment is computed by the processing module 4 based on the measured impedance value.

In this embodiment, the analyzer 2 is for example the analyzer Agilent 4294A coupled to Kelvin clip 16089A. This instrument works in the frequency range of 100 Hz-100 kHz, at a voltage of 0.5V. This reduction on the frequency is possible due to the steady state that CA showed in FIG. 8.

This method has been experimented by using the same sensor as for the first embodiment.

During experiments, impedance values between facing electrodes and coplanar electrodes of two adjacent pairs of facing electrodes 11 in contact with the CA layer in a same hole 12 were measured, that means 4 measurements:

- 1 measurement between the electrodes of the first pair of facing electrodes 11;
- 1 measurement between the electrodes of the second pair of facing electrodes 11;
- 1 measurement between the electrodes of the first pair of coplanar electrodes 11; and
- 1 measurement between the electrodes of the second pair of coplanar electrodes 11.

For both couples of measurements, impedance shows an inversely behaviour against chloride concentration, that is, the impedance value decreases as chloride concentration increases.

Table 2 lists the experiments for the calibration process, and Table 3 shows the randomization of those experiments. The solutions concentration varies between 0% and 6% w of $Cl^-/w$ of total solution, and one of the sensors was made empty (NCA) for demonstrating the design suitability. Solutions were directly applied to the holes 14 using rubber tubes and syringes, and two parallel capacitors (between facing electrodes) and only one coplanar capacitor (between coplanar electrodes) were measured in each chamber (hole 12 filled with the CA layer) due to the time of measurement (20 sec aprox.). The main objectives of this design are to determine linearity, time response and sensitivity. Each solution shown in Table 3 was made 4 times. In total, we used 22 devices, 4 repetitions, and 13 measurements over time. Additionally, at the beginning of the experiments we took the impedance of the dried CA.

TABLE 2

Design of Experiment for calibration

| [Cl-] | NC | t 2 t | 4 t | 6 t | 8 t | 1 t | 1 t | 2 t | 2 t | 3 t | 4 t1 | 5 t1 | 6 t1 | 9 t1 |
|---|---|---|---|---|---|---|---|---|---|---|---|---|---|---|
| 0,0 | C | C1t | C1t | C1t | C1t | C1t | C1t | C1t | C1t | C1t | C1t1 | C1t1 | C1t1 | C1t1 |
| 0,0 | C | C2t | C2t | C2t | C2t | C2t | C2t | C2t | C2t | C2t | C2t1 | C2t1 | C2t1 | C2t1 |
| 0,0 | C | C3t | C3t | C3t | C3t | C3t | C3t | C3t | C3t | C3t | C3t1 | C3t1 | C3t1 | C3t1 |
| 0,0 | C | C4t | C4t | C4t | C4t | C4t | C4t | C4t | C4t | C4t | C4t1 | C4t1 | C4t1 | C4t1 |
| 0,0 | C | C5t | C5t | C5t | C5t | C5t | C5t | C5t | C5t | C5t | C5t1 | C5t1 | C5t1 | C5t1 |
| 0,0 | C | C6t | C6t | C6t | C6t | C6t | C6t | C6t | C6t | C6t | C6t1 | C6t1 | C6t1 | C6t1 |
| 0,0 | C | C7t | C7t | C7t | C7t | C7t | C7t | C7t | C7t | C7t | C7t1 | C7t1 | C7t1 | C7t1 |
| 0,0 | C | C8t | C8t | C8t | C8t | C8t | C8t | C8t | C8t | C8t | C8t1 | C8t1 | C8t1 | C8t1 |
| 0,0 | C | C9t | C9t | C9t | C9t | C9t | C9t | C9t | C9t | C9t | C9t1 | C9t1 | C9t1 | C9t1 |
| 0,0 | C1 | C10t | C10t | C10t | C10t | C10t | C10t | C10t | C10t | C10t | C10t1 | C10t1 | C10t1 | C10t1 |
| 0,1 | C1 | C11t | C11t | C11t | C11t | C11t | C11t | C11t | C11t | C11t | C11t1 | C11t1 | C11t1 | C11t1 |
| 0,2 | C1 | C12t | C12t | C12t | C12t | C12t | C12t | C12t | C12t | C12t | C12t1 | C12t1 | C12t1 | C12t1 |
| 0,3 | C1 | C13t | C13t | C13t | C13t | C13t | C13t | C13t | C13t | C13t | C13t1 | C13t1 | C13t1 | C13t1 |
| 0,4 | C1 | C14t | C14t | C14t | C14t | C14t | C14t | C14t | C14t | C14t | C14t1 | C14t1 | C14t1 | C14t1 |
| 0,5 | C1 | C15t | C15t | C15t | C15t | C15t | C15t | C15t | C15t | C15t | C15t1 | C15t1 | C15t1 | C15t1 |
| 1,0 | C1 | C16t | C16t | C16t | C16t | C16t | C16t | C16t | C16t | C16t | C16t1 | C16t1 | C16t1 | C16t1 |
| 1,5 | C1 | C17t | C17t | C17t | C17t | C17t | C17t | C17t | C17t | C17t | C17t1 | C17t1 | C17t1 | C17t1 |
| 2,0 | C1 | C18t | C18t | C18t | C18t | C18t | C18t | C18t | C18t | C18t | C18t1 | C18t1 | C18t1 | C18t1 |
| 2,5 | C1 | C19t | C19t | C19t | C19t | C19t | C19t | C19t | C19t | C19t | C19t1 | C19t1 | C19t1 | C19t1 |

TABLE 2-continued

Design of Experiment for calibration

| | t | 2 | 4 | 6 | 8 | 1 | 1 | 2 | 2 | 3 | 4 | 5 | 6 | 9 |
|---|---|---|---|---|---|---|---|---|---|---|---|---|---|---|
| 3,0 | C2 | C20t | C20t | C20t | C20t | C20t | C20t | C20t | C20t | C20t | C20t1 | C20t1 | C20t1 | C20t1 |
| 6,0 | C2 | C21t | C21t | C21t | C21t | C21t | C21t | C21t | C21t | C21t | C21t1 | C21t1 | C21t1 | C21t1 |

TABLE 3

Randomization of experiment

| Random. | | [Cl−] (% w of Cl−/w of total solution) |
|---|---|---|
| C7 | 0.021 | 0.06 |
| C10 | 0.075 | 0.09 |
| C9 | 0.120 | 0.08 |
| C12 | 0.141 | 0.20 |
| C8 | 0.290 | 0.07 |
| C6 | 0.305 | 0.05 |
| C15 | 0.337 | 0.50 |
| C17 | 0.439 | 1.50 |
| C1 | 0.501 | 0.00 |
| C18 | 0.525 | 2.00 |
| C13 | 0.548 | 0.30 |
| C14 | 0.551 | 0.40 |
| C19 | 0.582 | 2.50 |
| C16 | 0.584 | 1.00 |
| C4 | 0.603 | 0.03 |
| C2 | 0.671 | 0.01 |
| C3 | 0.727 | 0.02 |
| C5 | 0.730 | 0.04 |
| C0 | 0.739 | NCA |
| C20 | 0.766 | 3.00 |
| C11 | 0.819 | 0.10 |
| C21 | 0.941 | 6.00 |

Figure 13:
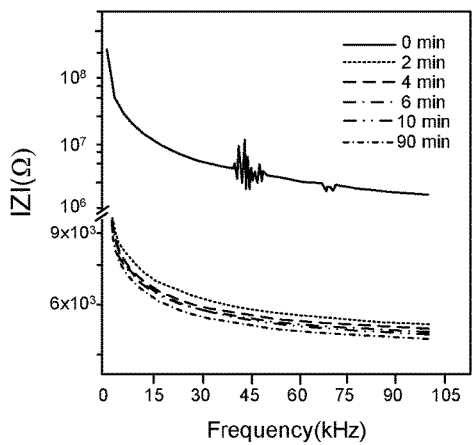
FIGS. 13 and 14 show curves illustrating the impedance magnitude and the phase angle versus time of the CA layer exposed to 0.50% w of Cl$^-$/w of total solution between two coplanar electrodes.
Figure 14:
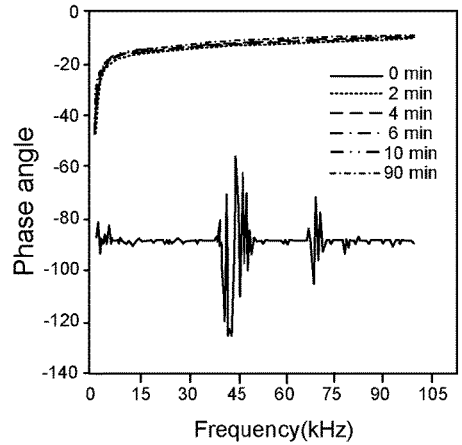

FIG. 13 shows the behaviour of the impedance and phase angle of a sensor with CA layer exposed to 0.50% w of Cl−/w of total solution, these measurement values being taken between coplanar electrodes. At minute 0 the CA was dry, and its phase angle shows its capacitive character ($\approx -90°$). However, when the solution interacts with the CA, its angle phase changes until it reaches $-5°$. It means that CA is not a pure capacitor anymore, but also an electrical resistor.

On the other hand, the magnitude of the impedance shows that its impedance decreases from $10^8$ to $10^3 \Omega$ in order of magnitude when the chloride solution reacts with the aluminate. These results are consistent with the results of the study disclosed in "Study of the dielectric properties in the NaNbO3-KNbO3-In2O3 system using AC impedance spectroscopy", E. Atamanik and V. Thangadurai, 2009, Materials Research Bulletin 44 (4):931-936. In this study, the behaviour of capacitance and impedance of different ceramic materials are analysed. In the end, the dielectric permittivity is defined by the following equations:

$$\varepsilon = \varepsilon' + j\varepsilon'' \quad (2)$$

$$\varepsilon' = \frac{z''}{2\pi f \varepsilon_0 S d Z^2} \quad (3)$$

$$\varepsilon'' = \frac{z'}{2\pi f \varepsilon_0 S d Z^2} \quad (4)$$

wherein $\varepsilon'$ and $\varepsilon''$ are real and imaginary parts of the dielectric permittivity;

Z, Z' and Z'' are the magnitude, real and imaginary parts of impedance;

S is the area exposed to CA of the electrodes, d is the distance between the electrodes, f is the frequency, and $\varepsilon_0$ is the dielectric constant of the vacuum ($8,8542 \times 10^{-12}$ C$^2$/Nm$^2$).

As equations (3) and (4) demonstrate, dielectric permittivity is inversely related to impedance, which is coherent with the previous results.

In contrast, parallel plate capacitors (between facing electrodes) of the same chamber (same hole 12 filled with the CA layer) show different results illustrated by FIGS. 15 to 18.

Figure 15:
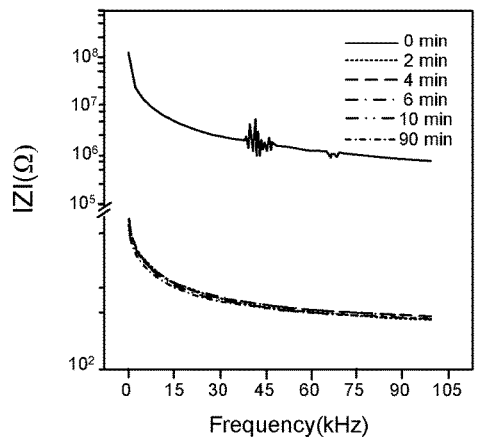
FIGS. 15 and 16 show curves illustrating respectively the impedance magnitude |Z| and the phase angle versus time of the CA layer exposed to 0.50% w of Cl⁻/w of total solution between the electrodes of a first couple of facing electrodes.
Figure 16:
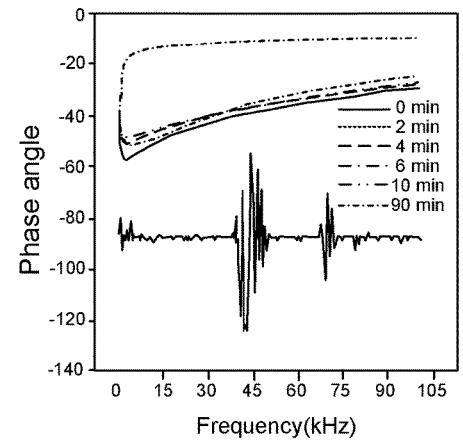
Figure 17:
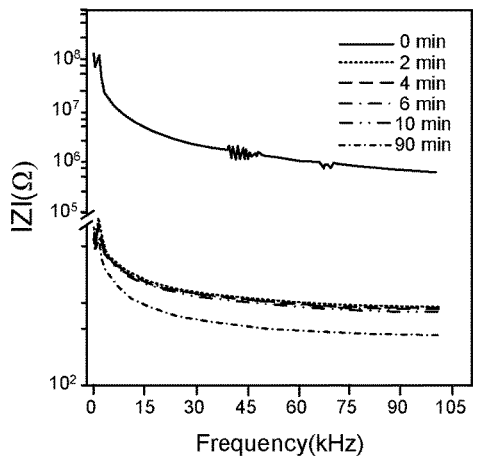
FIGS. 17 and 18 show curves illustrating respectively the impedance magnitude |Z| and the phase angle versus time of the CA layer exposed to 0.50% w of Cl⁻/w of total solution between the electrodes of a second couple of facing electrodes.
Figure 18:
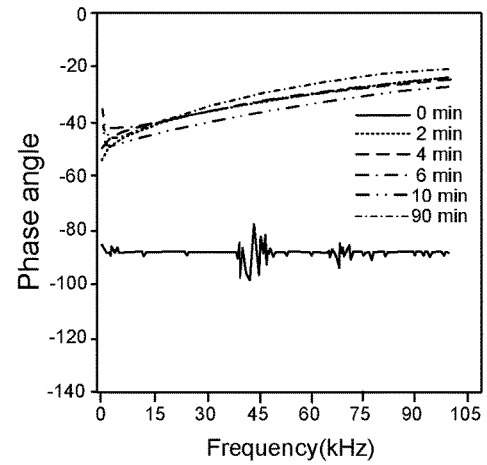

FIG. 15 and FIG. 16 represent Bode diagrams of the impedance value |Z| and the phase angle of a first pair of facing electrodes separated by a CA layer exposed to 0.50% w of Cl−/w of total solution (first parallel capacitor). FIG. 17 and FIG. 18 represent the same diagrams for a second pair of facing electrodes separated by the same CA layer exposed to 0.50% w of Cl−/w of total solution (second parallel capacitor).

Even when both parallel capacitors have the same changes as the coplanar capacitor (Resistive behaviour for the coplanar capacitor and Capacitive behaviour for the parallel capacitors), at the end of the experiment, parallel capacitors do not reach a quasi-perfect resistive behaviour as aluminate in the coplanar plate capacitor does (see FIG. 16 and FIG. 18). In addition, the impedance magnitude changes over time in one of the capacitors while in the other the impedance reaches a steady state during the experiment (FIG. 15 and FIG. 17). This difference could be explained by differences in the diffusion process.

That is the reason, in this embodiment with impedance measurement, the impedance is preferably measured between coplanar electrodes.

Figure 19:
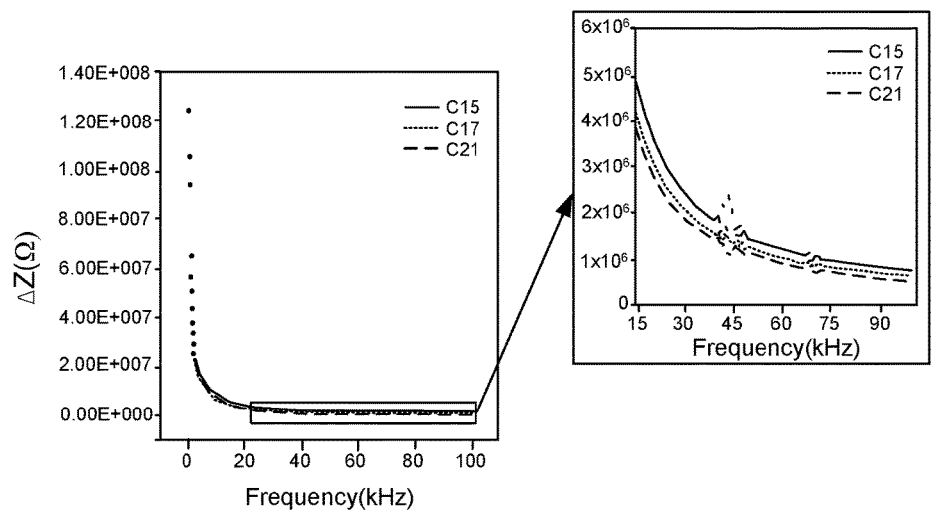
FIG. 19 shows curves illustrating the impedance difference $\Delta Z$ between dried CA and CA exposed to different NaCl solutions, measured between two coplanar electrodes, versus frequency.

Preliminary results show that impedance difference ($\Delta Z$) between initial dried CA ($Z_0$) and CA exposed to solutions (0.5, 1.5, and 6.0% w of Cl−/w of total solution) reach a steady state after 15 kHz as illustrated by FIG. 19 for coplanar electrodes. $\Delta Z$ is calculated by following:

$$\Delta Z = Z - Z_0 \quad (4)$$

In addition, there are some ranges where the response signal shows a considerable noise: 37.6-52 kHz and 65.1-80.9 kHz. These ranges must or should be avoided for measuring the impedances. Consequently, the measurements are advantageously made in the following ranges:

16 kHz<f<37.5 kHz 52 kHz<f<65 kHz 81 kHz<f<99 kHz

Figure 20:
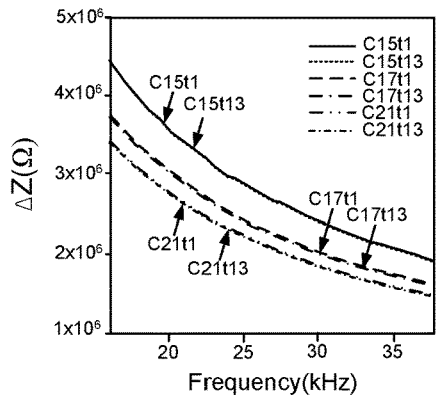
FIG. 20 shows curves illustrating the impedance difference $\Delta Z$ versus frequency in the frequency range [16 kHz; 37.5 kHz] at two different times t1 and t13.
Figure 21:
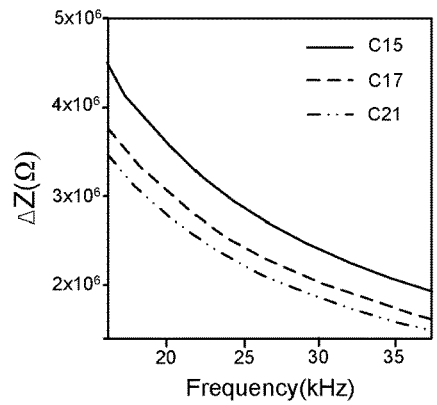
FIG. 21 shows curves illustrating the time average impedance difference $\Delta Z$ versus frequency in the frequency range [16 kHz; 37.5 kHz]
Figure 22:
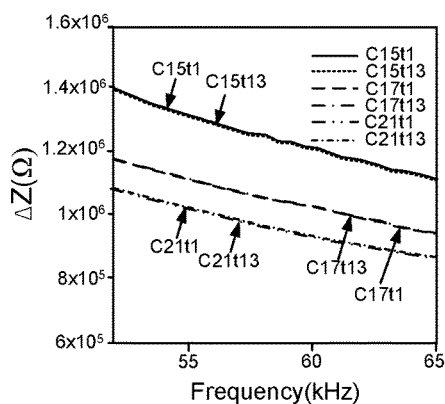
FIG. 22 shows curves illustrating the impedance difference $\Delta Z$ versus frequency in the frequency range [52 kHz; 65 kHz] at two different times t1 and t13.
Figure 23:
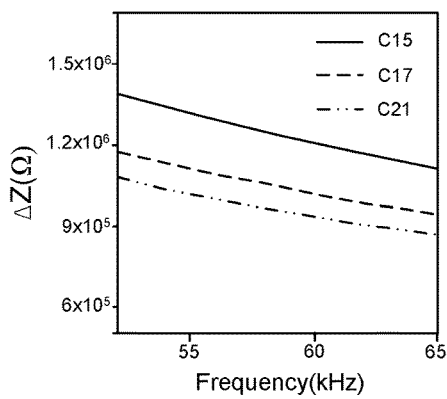
FIG. 23 shows curves illustrating the time average impedance difference $\Delta Z$ versus frequency in the frequency range [52 kHz; 65 kHz]
Figure 24:
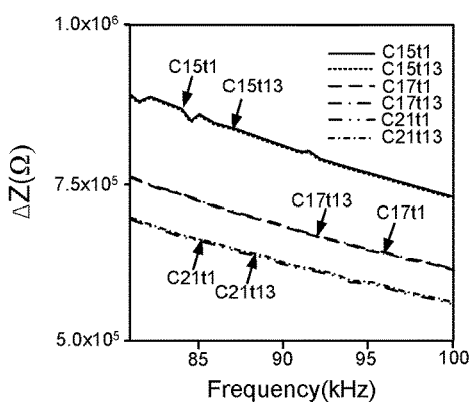
FIG. 24 shows curves illustrating the impedance difference $\Delta Z$ versus frequency in the frequency range [81 kHz; 99 kHz] at two different times t1 and t13.
Figure 25:
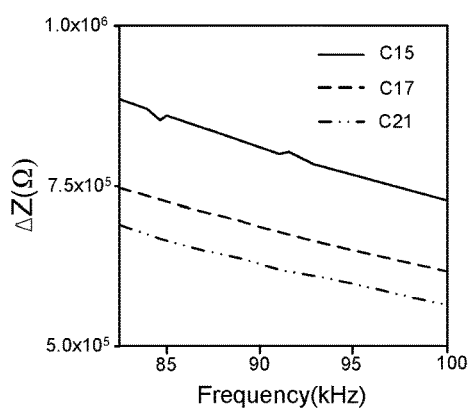
FIG. 25 shows curves illustrating the time average impedance difference $\Delta Z$ versus frequency in the frequency range [81 kHz; 99 kHz].

Additionally, regarding the time response, we can note that there is not a significant difference between the final impedance difference at 90 min (t13) and the first impedance difference at 2 min (t1) as illustrated by FIGS. 20 to 25. FIG. 20 represents the impedance difference $\Delta Z$ versus Frequency in the frequency range [16 kHz; 37.5 kHz] for C15t1, C15t13, C17t1, C17t13, C21t1, C21t13, and FIG. 21 represents the time average impedance difference value over time t1 to t13 for C15, C17 and C21. FIGS. 22-23 and FIGS. 24-25 represent the same diagrams for the frequency ranges [52 kHz; 65 kHz] and [81 kHz; 99 kHz], respectively.

These curves (FIGS. 20 to 25) show that the frequency ranges [16 kHz; 37.5 kHz], [52 kHz; 65 kHz] and [81 kHz; 99 kHz] are the most appropriate ones for the alternate current when measuring the impedance between coplanar electrodes. The chloride concentration can be assessed from the measured impedance between coplanar electrodes in these frequency ranges of the alternate current.

Some of the major advantages of the above described methods and systems are:
- the sensor is chemically stable (alkalinity inside concrete),
- the sensor can withstand temperatures and mechanical stresses,
- the sensor does not need extra protection, since the housing can isolate the inner material from corrosive environment,
- the sensor can be placed anywhere, near a corner,
- the measurements are not affected by the presence of electrical fields,
- its construction is cheap.

Of course, it may not be necessary that the chloride sensor 1 includes both facing electrodes and coplanar electrodes for a same chamber filled with calcium aluminate. If the method based on capacitance measurement is used, a sensor with only facing electrodes on both sides of the chamber is sufficient. If the method based on impedance measurement is used, a sensor with only facing electrodes on both sides of the chamber or coplanar electrodes on one side of the chamber is sufficient.

Although some embodiments of the present invention have been illustrated in the accompanying Drawings and described in the foregoing Detailed Description, it should be understood that the present invention is not limited to the disclosed embodiments, but is capable of numerous rearrangements, modifications and substitutions without departing from the invention as set forth and defined by the following claims.

The invention claimed is:

1. A system for assessing chloride ions concentration at one predetermined area of a porous or composite material, the system comprising:
   a sensor embedded in the one predetermined area,
   an analyzer connected to the sensor, and
   a processor connected to the analyzer,
   wherein the sensor includes two facing or coplanar flat electrodes, an intermediate layer arranged between the two electrodes, the intermediate layer being in contact with the material of the predetermined area and including calcium aluminates,
   wherein the analyzer is configured to apply an alternate current between the two electrodes and output an impedance value or capacitance value of the intermediate layer, and
   wherein the processor is configured to compute a chloride ions concentration assessment in the predetermined area based on the impedance value or capacitance value outputted by the analyzer.

2. The system according to claim 1, wherein the two electrodes are facing electrodes, and wherein the analyzer is configured to output a capacitance value and wherein, for computing the chloride ions concentration assessment in the predetermined area, the processor is configured to compute a relative permittivity value of the intermediate layer between the two electrodes from the capacitance value outputted by the analyzer and to compute the chloride ions concentration assessment in the predetermined area based on the computed relative permittivity value.

3. The system according to claim 2, wherein the frequency of the alternate current is included in a range of 100 Hz to 5 MHz.

4. The system according to claim 1, wherein the analyzer is configured to measure an impedance value between the two electrodes, by applying an alternate current between the two electrodes, and the processor is configured to compute the chloride ions concentration assessment in the predetermined area based on the measured impedance value.

5. The system according to claim 4, wherein the two electrodes are coplanar electrodes.

6. The system according to claim 4, wherein the frequency of the alternate current is included in the following group of frequency ranges of 100 Hz to 100 kHz, 16 kHz to 37.5 kHz, 52 kHz to 65 kHz, and 81 kHz to 99 kHz.

7. A method for assessing chloride ions concentration in a predetermined area of a porous or composite material, by using a sensor embedded in the predetermined area, the sensor including two facing or coplanar flat electrodes, an intermediate layer arranged between the two electrodes, the intermediate layer being in contact with the material of the predetermined area and including calcium aluminates,
   the method comprising:
      measuring a capacitance value or an impedance value of the intermediate layer by applying an alternate current between the two electrodes; and
      computing a chloride ions concentration assessment in the predetermined area based on the measured impedance value or capacitance value.

8. The method according to claim 7, wherein the two electrodes are facing electrodes, and the measured value is a capacitance value of the intermediate layer between the two electrodes, and wherein the chloride ions concentration assessment is computed by:
   computing a relative permittivity value of the intermediate layer between the two electrodes, and
   computing the chloride ions concentration assessment in the predetermined area based on the computed relative permittivity value.

9. The method according to claim 8, wherein the frequency of the alternate current is included in a range of 100 Hz to 5 MHz.

10. The method according to claim 7, wherein the measured value is an impedance value of the intermediate layer between the two electrodes, and wherein the chloride ions concentration assessment is computed based on the measured impedance value.

11. The method according to claim 10, wherein the two electrodes are coplanar electrodes.

12. The method according to claim 11, wherein the frequency of the alternate current is included in the following group of frequency ranges of 100 Hz to 100 kHz, 16 kHz to 37.5 kHz, 52 kHz to 65 kHz, and 81 kHz to 99 kHz.

13. A chloride ions sensors to be embedded in a predetermined area of a porous or composite structure, comprising:
   a housing,
   at least two facing or coplanar flat electrodes within the housing,
   an intermediate layer arranged between the two electrodes within the housing, the intermediate layer being in contact, via at least one hole in the housing, with the material of the predetermined area and including calcium aluminates, and pin connectors connected to the two electrodes via conductive lines and arranged for connecting the two electrodes to an external device.

14. The chloride ions sensors according to claim 13, further including a plurality of pairs of electrodes offset with respect to one another along an axis of the sensor, and connected to a plurality of pin connectors, an intermediate layer being arranged between the two electrodes of each pair of electrodes, and at least a hole being arranged in the housing at the proximity of each pair of electrodes and opening into the intermediate layer.

15. The chloride ions sensors according to claim 13, wherein the calcium aluminates are selected from the group of:
CA,
$C_3A$,
$C_{12}A_7$.

16. The chloride ions sensors according to claim 13, wherein the material of the housing is fiber glass or Bakelite or ceramic or Teflon.

17. The system according to claim 5, wherein the frequency of the alternate current is included in the following group of frequency ranges of 100 Hz to 100 kHz, 16 kHz to 37.5 kHz, 52 kHz to 65 kHz, and 81 kHz to 99 kHz.

18. The chloride ions sensors according to claim 14, wherein the calcium aluminates are selected from the group of:
CA,
$C_3A$,
$C_{12}A_7$.

19. The chloride ions sensors according to claim 14, wherein the material of the housing is fiber glass or Bakelite or ceramic or Teflon.

20. The chloride ions sensors according to claim 15, wherein the material of the housing is fiber glass or Bakelite or ceramic or Teflon.

* * * * *